United States Patent [19]

Augustine et al.

[11] Patent Number: 4,840,172
[45] Date of Patent: Jun. 20, 1989

[54] DEVICE FOR POSITIONING AN ENDOTRACHEAL TUBE

[76] Inventors: Scott D. Augustine, 4761 Olive St., San Diego, Calif. 92105; Douglas J. Augustine, Box 37, Sandstone, Minn. 55072

[21] Appl. No.: 119,300

[22] Filed: Nov. 6, 1987

Related U.S. Application Data

[63] Continuation of Ser. No. 904,011, Sep. 4, 1986, abandoned.

[51] Int. Cl.⁴ .............................................. A61M 16/00
[52] U.S. Cl. ............................... 128/207.14; 604/284; 604/164; 604/170
[58] Field of Search ..................... 128/207.17, 207.18, 128/266.26, 328, 341, 345, 343, 657; 604/164–167, 281, 282, 284, 164, 170

[56] References Cited

U.S. PATENT DOCUMENTS

| 3,792,701 | 2/1974 | Kloz et al. ............... | 128/328 |
| 3,799,173 | 3/1974 | Kamen ..................... | 128/207.15 |
| 4,043,346 | 8/1977 | Molsley et al. ........... | 604/107 |
| 4,393,872 | 7/1983 | Reznik et al. ............ | 604/106 |

FOREIGN PATENT DOCUMENTS

| 86/02848 | 5/1986 | PCT Int'l Appl. ......... | 128/207.15 |
| 124593 | 3/1959 | U.S.S.R. ................. | 128/207.14 |
| 199338 | 9/1967 | U.S.S.R. ................. | 128/207.18 |
| 908371 | 2/1982 | U.S.S.R. ................. | 128/207.15 |
| 2098485 | 1/1982 | United Kingdom ........ | 128/207.18 |

Primary Examiner—Edward M. Coven
Assistant Examiner—K. M. Reichle
Attorney, Agent, or Firm—Baker, Maxham, Jester & Meador

[57] ABSTRACT

A device for positioning an endotracheal tube when the tube is inserted into the trachea of a patient for lung inflation uses the patient's carina as a reference point against which the endotracheal tube is positioned. The positioning device consists of an elongate, flexible member with at least three flexible filaments at its distal end which assume a compressed tripodal configuration when inserted through the endotracheal tube. When the distal end of the positioning device emerges from the distal end of the endotracheal tube, the flexible elements spring out into a tripodal-shaped structure. As the positioning device is advanced further, the apex of the tripodal-shaped structure engages the carina. At this point the positioning device provides a reference line for correctly locating the distal end of the endotracheal tube with respect to the carina. Since the dimensions of the positioning device and the endotracheal tube are known, the location of the distal end of the tube with respect to the carina can be indirectly derived by observing the position of the tube with respect to the positioning device. The relative measurement is provided by calibration marks at the proximal end of the positioning device. Once the endotracheal tube is correctly positioned in the trachea, the positioning device can be withdrawn. The tripodal-shaped structure is compressed when the distal end of the positioning device enters the distal end of the endotracheal tube lumen. The positioning device is then removed to allow ventilation of the patient through the endotracheal tube.

9 Claims, 2 Drawing Sheets

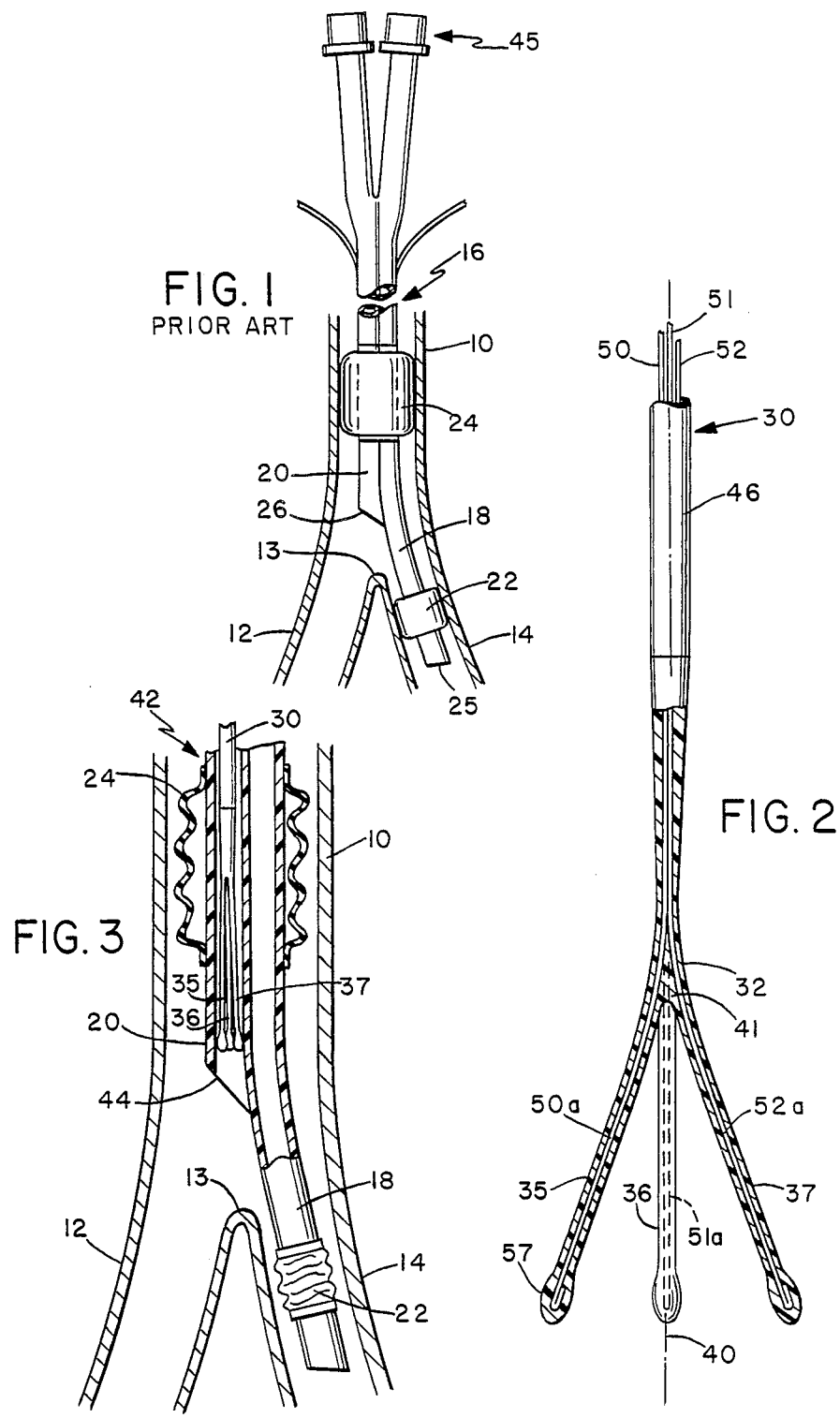

DEVICE FOR POSITIONING AN ENDOTRACHEAL TUBE

This is a continuation of application Ser. No. 904,011 filed Sept. 4, 1986, now abandoned.

BACKGROUND OF THE INVENTION

This invention relates to a device for positioning an endotracheal tube in the trachea with respect to the carina, and more particularly regards a positioning device with a carina-engaging stop consisting of three flexible extensions which form a tripodal configuration.

Intubation of the the trachea with a double-lumen catheter for the purpose of selective ventilation of the lung is known in the art. For example, a double-lumen tube, illustrated in FIG. 1, is inserted into the trachea 10 for selective inflation of the lungs through the left and right bronchi 12 and 14, respectively. The double-lumen tube 16 includes a left bronchial tube 18, a tracheal tube 20, a bronchial cuff 22, and a tracheal cuff 24. The bronchial cuff is mounted on the left bronchial tube near the tube's distal end 25. The tracheal cuff surrounds both the bronchial and tracheal tubes near the distal end 26 of the tracheal tube. The left bronchial tube is slightly curved near its distal end 25.

The double-lumen tube 16 is used by inserting the two distal ends 25 and 26 into the trachea 10 with the distal curvature of the bronchial tube 22 to the left and parallel to the surface supporting the patient. The tube is inserted until the bronchial cuff 22 enters the left bronchus 12. At this point, the tube 16 is properly positioned and the cuffs 22 and 24 are inflated. Now, either lung individually or both lungs together can be inflated through the distal ends 25 and 26 of the tube 16.

In order for the endotracheal tube 16 to be correctly operated, it must be precisely positioned so that the tracheal cuff 24 is not inserted so far down into the trachea as to seal off the right main bronchus, thereby preventing inflation of the right lung. Further, if the tube 16 is not inserted far enough, the bronchial cuff 22, when inflated, can distend over the carina 13 into the right bronchus, thereby providing an imperfect seal of the left bronchus and partially occluding the right bronchus.

Practitioners skilled in the art of using double-lumen endotracheal tubes know that the correct operation of a double-lumen tube will be assured if the cuffs 22 and 24 are correctly positioned with regard to the carina 13. In this regard, the tracheal cuff 24 must be positioned cefelad or proximal to the bronchial bifurcation marked by the carina 13, while the bronchial cuff 22 must be positioned within the left bronchus, downwardly displaced in the bronchus with respect to the carina 13.

Conventionally, correct positioning of an endotracheal tube in the trachea is done with respect to the carina 13, which provides a clearly distinguishable reference point in the tracheal complex. Positioning of the tube and assessment of lung inflation is typically accomplished with bilateral ausculation of the chest with a stethoscope during unilateral ventilation. This method is notoriously difficult and inaccurate for reliably determining the tube's position. Positioning can also be assessed by the aid of an X-ray apparatus. However, the limitations of an X-ray apparatus are well known. Such apparatus is large and static and does not always provide the resolution necessary for precise positioning. Fiber optic endoscopes are also used for positioning endotracheal tubes. However, such devices are expensive, fragile, and require the use of a trained expert for their operation.

Another means for positioning an endotracheal tube is disclosed in U.S. Pat. No. 4,449,522 of Baum. The Baum positioning device consists of a flexible probe having a pair of foldable arms at its distal end which are folded outwardly from the end of the device when it is inserted through an endotracheal tube initially positioned in the trachea. The outward folding of the device arms is effected by an actuating wire which extends through the device to its near end where it can be operated by a user. When operated by a user, the actuating device unfolds the pair of arms into a V-shaped structure which engages the carina when the positioning device is slid further forward through the endotracheal tube. The positioning device of the Baum patent has certain drawbacks. First, the device is complex and relatively expensive to manufacture, requiring a manually-operated actuating mechanism as an essential part. Next, the carina-engaging portion of the device consists specifically of two arms. It will be evident to the skilled practitioner that if the span of the V-shaped structure formed when the two arms are unfolded is not substantially perpendicular to or does not lie across the carina, the carina might not be engaged and the distal end of the device can track down one bronchus or the other. Third, the arms are foldable, which means that their combined length when each is rotated to the 90° position with respect to the trachea must be less than the diameter of the trachea. Since the arms are further unfolded through that 90° position into a forwardly-angled position to engage the carina, the diameter described by the span of the arms is obviously less than the diameter of the trachea. Thus, in the actuated position, the arms can miss the carina and fit into a bronchus. Further, the actuating force for the arms is directed inwardly, so the design precludes the arms "tracking down" the wall of the trachea to engage the carina. When this device is in the folded position, it requires the folded arms to assume a streamlined profile in order to fit alongside the main element and yet fit within the endotracheal tube. This profile precludes placing rounded, slightly bulbous tips on the arms to prevent penetration of and damage to the tracheal wall. Additionally, each arm must be rotated through an angle of substantially greater than 90° in a direction posing a risk of trauma to the interior surface of the trachea.

Therefore, in view of the conventional means for positioning an endotracheal tube, it is evident that there is a need for an inexpensive, easily-operated device which accurately, reliably and safely positions an endotracheal tube.

SUMMARY OF THE INVENTION

It is the principal objective of the invention to provide for positioning an endotracheal tube in a trachea by a device which reliably and accurately engages the carina, while minimizing the risk of injury to the interior surface of the trachea.

This objective is achieved in the present invention by the critical observation that use of a spring-biased tripodal carina-engaging structure at the distal end of a positioning member insertable through an endotracheal tube will assure that the carina is reliably and safely engaged, no matter what the rotational orientation of the positioning device with respect to the carina. The outwardly-directed spring-bias of the structure permits it to be compressed for insertion into the endotracheal tube, yet automatically actuates the structure by springing it outwardly when the distal tip of the positioning device emerges from the distal end of the initially-positioned endotracheal tube.

From one aspect, the invention consists of a device for positioning an endotracheal tube in a trachea, which includes an elongate, flexible positioning member with distal and proximal ends that is slidably receivable within an endotracheal tube. The positioning member has length sufficient to permit its distal end to extend through the distal end of the endotracheal tube when the positioning member is received therein. A carina stop on the distal end of the positioning member includes three or more flexible extensions, each of which is spring-biased obliquely out from the axis of the positioning member. The three flexible extensions form a tripodal structure that springs outwardly from the axis of the positioning device when the distal end of the device protrudes through the distal end of the endotracheal tube.

From another aspect, the invention is expressed as a device for positioning an endotracheal tube in a trachea, with the positioning device including a tubular, elongate member having proximal and distal ends. Three or more elongate, flexible filaments are disposed in the member, each of the filaments having a flexible end which extends beyond the distal end of the member. The positioning device includes a biasing structure for imposing a permanent spring bias on each of the filament ends, which flexibly positions the filament end obliquely outward from the central axis of the positioning device and at a respective leg position of an equilateral tripodal structure extending beyond the distal end of the member.

Finally, the invention is embodied in an apparatus for intubating a trachea and includes an endotracheal tube with a distal end which is positionable within a trachea. An elongated, flexible positioning member with a distal end is slidably receivable within the endotracheal tube and is movable within the endotracheal tube between a first position in which the positioning member distal end is contained within the endotrachel tube, and a second position in which the positioning member distal end extends through the endotracheal tube distal end. A carina stop is provided on the positioning member distal end and includes three or more flexible extensions, each of which is spring-biased obliquely outward from the axis of the positioning member such that the three extensions form a tripodal structure which is retained in a compressed position by the endotracheal tube when the positioning member is at the first position and which is sprung by the spring bias of the flexible extensions outwardly from the positioning member distal end when the positioning member is at the second position.

It will become evident that these expressions of the invention meet the stated objective and provide other objects in advantages when the following detained description is read in connection with the below-described drawings.

BRIEF DESCRIPTION OF THE DRAWINGS

FIG. 1 illustrates the correct positioning of a double-lumen endotracheal tube with respect to a carina trachea.

FIG. 2 illustrates, partly in section, the distal end of the positioning device.

FIG. 3 illustrates, partly in section, the invention in a first position in the endotracheal tube of FIG. 1.

DESCRIPTION OF THE PREFERRED EMBODIMENT

Figure 5:
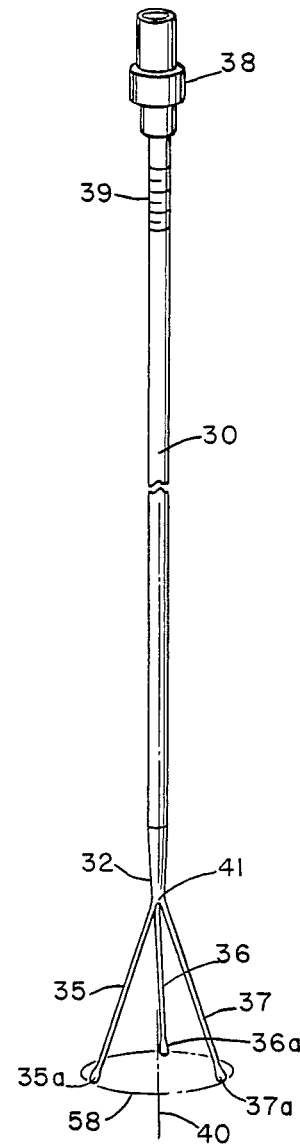
FIG. 5 illustrates structural details of the positioning device.

Referring now to the drawings, particularly FIGS. 2 and 5, the invention is seen as a device for positioning in the trachea tubes such as the endotracheal tube of FIG. 1. The device consists of a positioning member 30 having a distal end 32 which transitions into three flexible extension arms, 35, 36, and 37. The positioning member 30 also has a proximal end 38. A series of graduation markings 39 are made on the outside surface of the rear portion of the positioning member 30 substantially adjacent the proximal end 38, which correspond to the distance from the markings to the distal end of the member 30.

As shown in FIGS. 2 and 5, the flexible extensions 35, 36 and 37 are formed on the positioning member 30 at its distal end 32. Each of the flexible extensions is spring-biased in an outwardly oblique direction with respect to the central axis 40 of the positioning member 30. When unrestrained, the flexible extensions 35, 36 and 37 form an equilateral equiangular tripodal structure in which each of the extensions corresponds to one of three tripod legs. The tips 35a–37a of the flexible extensions are slightly enlarged and rounded. The legs of the tripodal structure are joined at a vertex 41 located at the distal tip 32. Because the flexible extensions are spring-biased, each is capable of being flexed inwardly toward the central axis 40.

Turning to FIG. 3, the positioning device 30 is seen to be slidably receivable in the tracheal lumen of a double-lumen endotracheal tube 42, which is shown disposed in the trachea 10, with the tracheal carina indicated by 13. In FIG. 3, the positioning member 30 is shown at a first position, where it is inserted, distal end first, into the tracheal lumen of the endotracheal tube 42. When the distal end of the positioning member 30 is inserted into the tracheal lumen 20 of the tube 42, the flexible extensions 35, 36 and 37 are flexed inwardly toward the central axis 40 of the positioning member forming a compressed configuration. The flexible extensions are retained in this closed position by the walls of endotracheal tube lumen. With the flexible extensions in the closed position, the distal end 32 of the positioning member 30 is advanced toward the distal end 44 of the tracheal lumen of the endotracheal tube 42.

Figure 4:
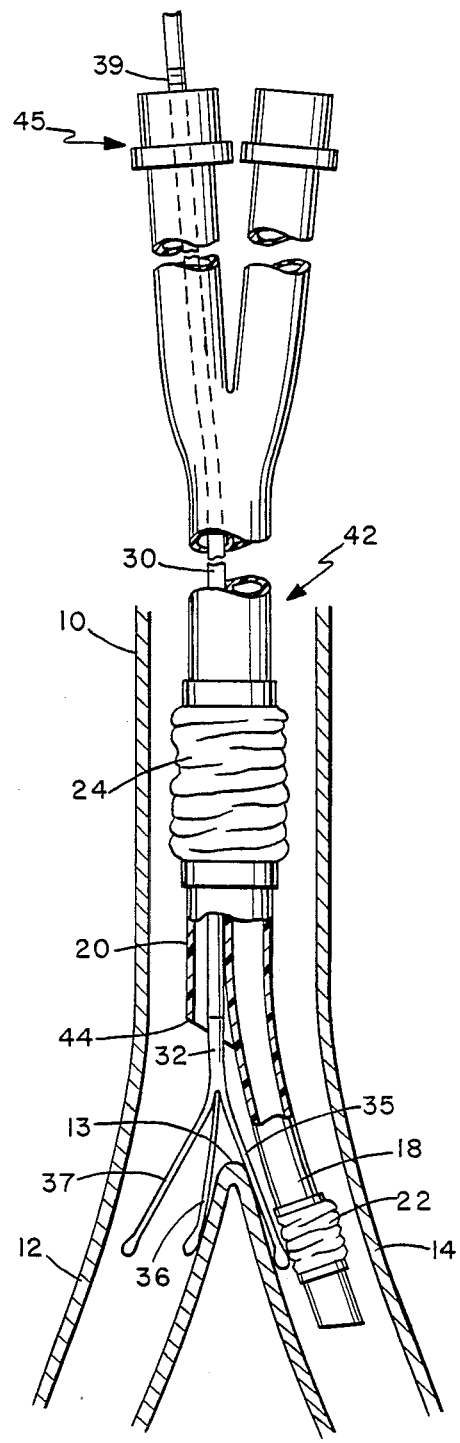
FIG. 4 illustrates, partly in section, the invention at a second position with respect to the endotracheal tube of FIG. 1 in which the tracheal carina is engaged in order to position the endotracheal tube.

In FIG. 4, the positioning member 30 is shown in a second position where the distal tip 32 has been advanced through the distal tip 44 of the endotracheal tube tracheal lumen. When the flexible extensions 35, 36 and 37 extend beyond the distal tip 44, their spring biases cause them to spring out into the tripodal structure illustrated in FIGS. 2, 4 and 5. The flared tripodal structure essentially forms a carina stop which engages the tracheal carina 13. Because the structure is tripodal, regardless of its orientation with respect to carina 13, a pair of flexible extensions will span the carina to engage it even if the positioning member is rotated about its axis. In this regard, if one of the extensions is in the vertical plane of the carina while the other two extensions span the carina, the flexibility of the one extension, together with its rounded tip and the frictional properties of the material from which it is formed, will assist in tracking the extension down one or the other of the sloped carina sides, thereby permitting the other two extensions, which span the carina, to engage the carina.

As the positioning member 30 is advanced further into the endotracheal tube 42, the tripodal structure comprising the flexible extensions emerges from the distal end 44 and engages the carina 13. With the carina thus engaged, the endotraceal tube 42 can be positioned correctly with respect to the tracheal carina by means of the graduation marks 39. In this regard, the length of the positioning member 30 is known, so the distance from the carina, where trachea branches into the bronchi, is known. It is assumed that the length of the endotracheal tube 42 is also known, so that the position of the tracheal lumen distal tip 44 with respect to the carina can be determined by observing the position of the proximal end 45 of the endotracheal tube with respect to the graduation markings 39 on the positioning member 30.

A specific structure of the positioning device can be understood with reference to FIGS. 2 and 5. The member 30 comprises a tube 46, composed of any available plastic material having the flexibility and coefficient of friction necessary to make the tube slidable within an endotracheal tube. Within the positioning member 30 are disposed three elongate filaments, 50, 51 and 52, which can comprise, for example, stainless steel filaments. The filaments are anchored to the interior of the tube 46 and extend along the interior of the tube through its distal tip 47. At the location of the distal tip 32 of the member 30, the filaments, 50, 51 and 52 are bound together by any convenient means such as, for example, a coiled copper wire, to form the vertex 41 of the tripodal structure. A permanent outward bend is made in each of the filaments at the vertex 41, with each filament being bent in alignment with one of the three legs of the equilateral tripodal structure. The bent ends of the filaments are indicated by 50a, 51a and 52a respectively. The assembly of filaments extending from the tube distal tip 47 is encapsulated in a flexible material; each of the bent filament ends is encapsulated separately from the other two. The encapsulation, being flexible, assists in retaining the bent filament ends in the tripodal structure, yet permits them to be flexed to the compressed position of FIG. 3. Further, the encapsulation adds to the spring bias of the filament ends and therefore, supplements the spring-like movement of the bent ends laterally away from the central axis 40 when they emerge from the distal end of an endotracheal tube. The encapsulation of the filament 50a is indicated by 57, it being understood that the other filament ends are identically encapsulated.

It should be evident to the skilled practitioner that the tube 46 can be formed by extrusion, with the encapsulation being later formed on the tube by, for example, a molding process. Alternatively, the tube and encapsulation can be molded in a single step.

It is shown in FIG. 5 that the tripodal structure compounded of the extensions 35, 36 and 37 intercepts a circle, 58. It should be evident that the diameter of the circle 58 can be adjusted during assembly of the positioning device in order to ensure that, when the flexible filament ends spring into the tripodal structure, they describe a circle which is at least equal to the diameter of the trachea of a patient to be intubated. This will ensure that the tripodal structure will span the tracheal carina of a patient by contacting the inner surface ofo the trachea. Yet the lengths of the extensions allow a flaring action that is outward from the central axis of the trachea through rotation of less than 90°. This, of course, reduces the prospect of injury to the inner surface of the trachea when the carina-engaging tripodal structure is flaring out. Further, it should be obvious that the length of the flexible extensions is not limited by the requirement that they be rotated from a folded position for engaging the carina. It will also be manifest that the enlarged rounded tips of the flexible extensions also attenuate the chance of penetration of or trauma to the wall of the trachea.

Obviously, many modifications and variations of this invention are possible in light of these teachings, and it is therefore understood that, within the scope of these teachings, it may be practiced otherwise than as specifically described.

We claim:

1. A device for positioning an endotracheal tube in a trachea of a patient to be intubated, comprising:
    an elongate flexible positioning member with an axis, a closed distal end and a proximal end;
    three elongated flexible extensions attached to said distal end and forming a tripodal structure with a vertex attached to and opening away from said distal end, said tripodal structure having a base which describes a circle having a predetermined diameter which is at least equal to the trachea diameter of the trachea of a patient to be intubated; and
    bias means in each of said extensions and acting solely between said extension and said distal end for moving said extension from a closed position along said axis, through an angle of less than 90°, to a respective leg position in said tripodal structure and for spring-biasing said extension to said leg position.

2. The device of claim 1 wherein each of said bias means is further for allowing each of said extensions to be moved through said angle in a direction toward said axis and away from said distal end.

3. The device of claim 1 wherein each of said extensions has an enlarged, rounded tip.

4. A device for positioning an endotracheal tube in a trachea of a patient to be intubated, comprising:
    an elongate, tubular positioning member having a central axis, a proximal end and a distal end;
    three elongate filaments disposed on and extending beyond said distal end, each of said filaments being movable through only an angle of less than 90°, toward said axis, and away from said distal end to form with the other filaments a closed tripodal structure extending outwardly from said member and away from said distal end; and
    bias means in said member adjacent said distal end and acting between said distal end and said filaments for imposing a permanent bias on each of said filaments which erects said filaments into an open tripodal structure having a vertex at and opening away from said distal end by moving each filament obliquely outward from said closed tripodal structure, through said angle, said open tripodal structure having a base which describes a circle having a predetermined diameter substantially equal to the trachea diameter of the trachea of a patient to be intubated.

5. The device of claim 4 wherein said bias means is further for allowing each of said filaments to be moved toward said axis.

6. An apparatus for intubating a trachea of a patient, comprising:

an endotracheal tube with a distal end;

an elongate, flexible positioning member with an axis and a distal end, said positioning member being slidably disposed within said endotracheal tube and movable within said endotracheal tube between a first position in which said positioning member distal end is contained within said endotracheal tube and a second position in which said positioning member distal end extends through said endotracheal tube distal end; and a carina stop on said positioning member distal end, said carina stop including three elongate flexible extensions and bias means for biasing each of said extensions obliquely out from the axis of said positioning member, said three extensions forming a tripodal structure having a vertex at and extending away from said distal end, said tripodal structure being retained in a compressed configuration by said endotracheal tube when said positioning member is at said first position and being flared by said bias means into an opened configuration when said positioning tube is at said second position, said bias means moving each of said extensions through an angle of less than 90° when placing said tripodal structure into said opened configuration, said opened configuration of said tripodal structure having a base which describes a circle having a predetermined diameter which is at least equal to the trachea diameter of the trachea of a patient to be intubated.

7. The apparatus of claim 6 wherein said bias means is further for allowing each of said extensions to be moved toward said axis and away from said positioning member.

8. The apparatus of claim 6 wherein each of said flexible extensions has an enlarged, rounded tip.

9. The apparatus of claim 6 wherein said endotracheal tube and said positioning member have respective proximal ends and said positioning member proximal end extends out through said endotracheal tube proximal end when said positioning member is at said first and second positions and further including graduation markings on said positioning member adjacent said positioning member proximal end for indicating the distance between said endotracheal tube and positioning member distal ends when said positioning member is at said second position, thereby accurately positioning said endotracheal tube with respect to a carina angaged by said carina stop.

* * * * *